United States Patent [19]

Page

[11] Patent Number: 4,706,301

[45] Date of Patent: Nov. 17, 1987

[54] BITE OPERATED VIEWPORT

[76] Inventor: Jefferson H. Page, Rte. 1, Box 31B, Autryville, N.C. 28318

[21] Appl. No.: 881,852

[22] Filed: Jul. 3, 1986

[51] Int. Cl.[4] .............................................. A61F 9/06
[52] U.S. Cl. .......................................................... 2/8
[58] Field of Search ........................... 2/8, 9, 432, 427

[56] References Cited

U.S. PATENT DOCUMENTS

| 1,885,744 | 11/1932 | Malcom | 2/8 X |
| 2,644,161 | 7/1953 | Meyer | 2/8 |
| 4,539,713 | 9/1985 | Hodge | 2/8 |

FOREIGN PATENT DOCUMENTS 0920269  11/1954  Fed. Rep. of Germany .............. 2/8

*Primary Examiner*—Peter Nerbun
*Attorney, Agent, or Firm*—Henry Huff

[57] ABSTRACT

A viewport for a welder's protective mask or the like, with a semitransparent window arranged to be opened by mandibular action of the user for inspection of a newly set weld, for example, while leaving both hands free to hold or manipulate other equipment.

1 Claim, 4 Drawing Figures

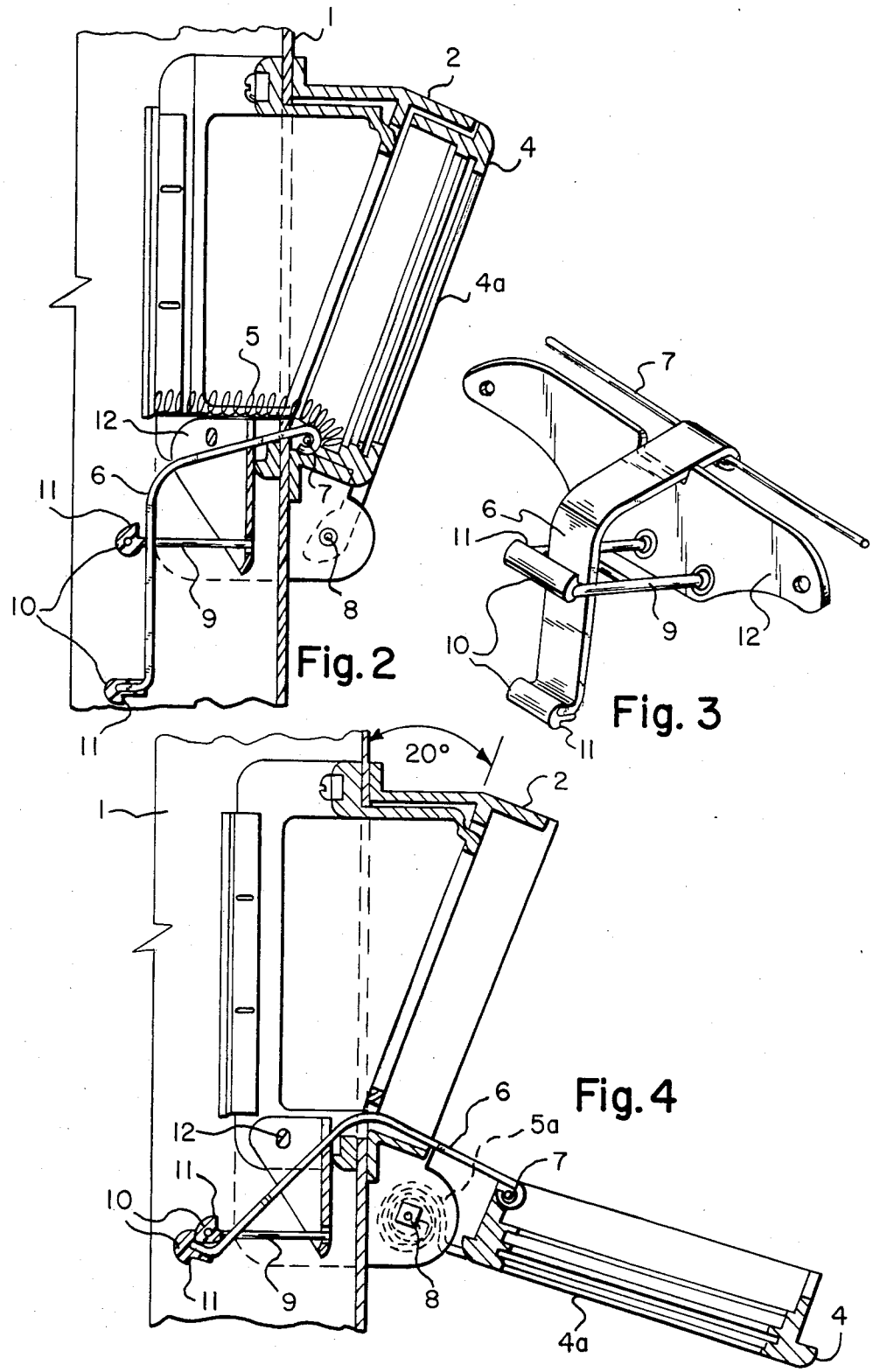

BITE OPERATED VIEWPORT

SUMMARY

This invention relates to improvements in protective face masks for welders, and more particularly to viewports for such masks with semitransparent windows that can be opened and closed by the wearer without the use of a hand or other body extremity.

Prior art facemasks are usually arranged to be tilted up over the wearer's head, either manually or by an abrupt jerk of the head, for viewing the work after a weld has been made. Some have been made with windows that can be opened, obviating the need to raise the entire mask. Such arrangements facilitate the inspection of a newly set weld, but require that the user have a hand or a finger free, or that he be in a position to move his head or some other extremity in a prescribed way. In many welding jobs, the operator must work in an awkward position or in a restricted space such that the needed movement is difficult or impossible.

The principal object of this invention is to provide a viewport arrangement without the foregoing disadvantages. Another object is to provide a viewport actuator that serves also to aid in retaining the mask in place even when the operator is in such a positiom, inverted, for example, that the mask may tend to fall off.

DRAWINGS

FIG. 2 is a side elevation, partly in section, of the viewport of FIG. 1 in its closed position.

FIG. 3 is an isometric view of the door actuating mechanism of FIGS. 1 and 2.

FIG. 4 is a side elevation, partly in section, of a modification of the structure of FIG. 2, showing the door in its open position.

DESCRIPTION

Figure 1:
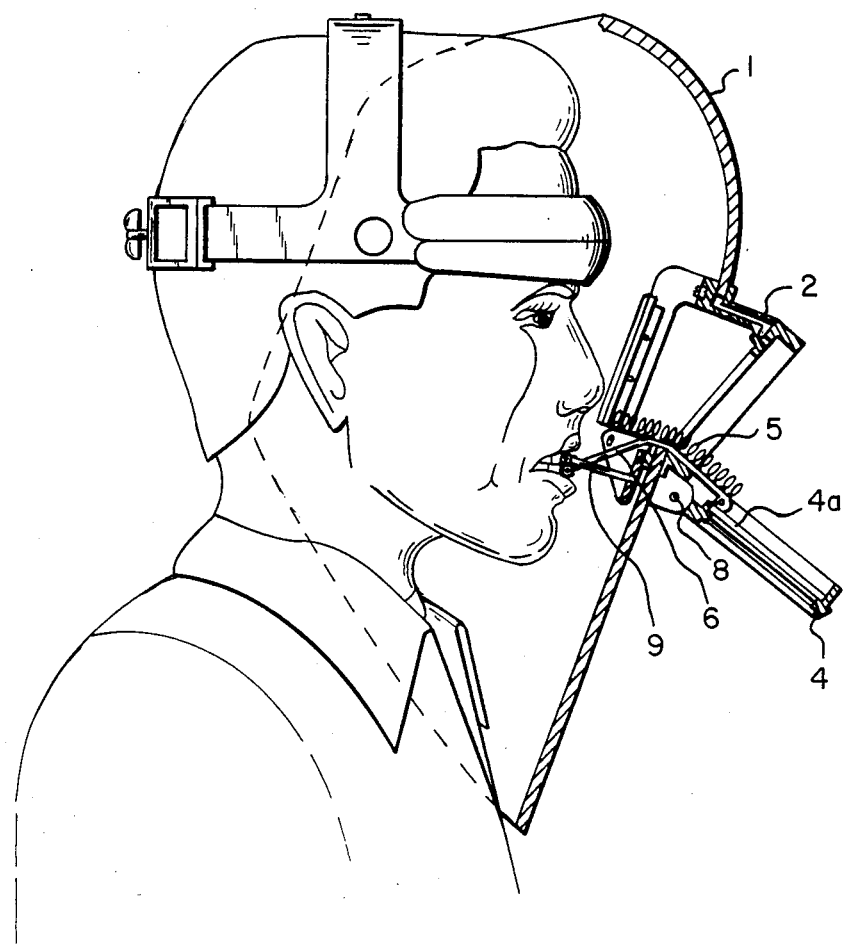
FIG. 1 is a pictorial view, partly in section, of a face mask including a presently preferred embodiment of the invention in use, with the viewport actuated to its open position.

Referring to FIG. 1, the helmet 1 of a conventional welder's face mask is shown secured on a welder by the usual headyoke. The usual fixed viewport window is replaced by a shell structure 2 surrounding the viewport opening and extending forwardly from the front of the mask or helmet 1, with a door 4 hingedly supported at its outer lower edge. The door 4 includes a semitransparent window 4a, and is shown in its open position, swung downward and outward from the hinge pin 8.

A tension spring 5, stretched between a point near the bottom edge of the door and a point near the bottom of the inner end of the housing 2, is arranged to bias the door 4 to its upper, closed position. As shown, the door is being held open by biting action of the user, applying opposed forces to a bite bar 9 and a linkage 6, illustrated more clearly in FIGS. 2, 3 and 4. The upper wall of shell structure 2 extends further from the front of the mask than the lower wall so that when the door is in its closed position the window 4a is tilted forward with respect to the front of the mask by about twenty degrees.

Referring to FIG. 2, the door 4 is shown held in its closed position by contraction of the tension spring 5. The linkage 6, with its upper end hinged on a pin 7 extending transversely at the bottom of the door, is in its lower position. The bite pads 10 may be made of any suitable semirigid plastic material, and arranged to be removable for cleaning and replacement. Ridges 11 are provided to facilitate engagement by the teeth of the user.

As shown in FIG. 3, the lower bite pad is secured to a structure 9 extending inwardly of the mask from a plate 12 shaped to conform to the inner front surface of the mask and fastened thereto by any appropriate means such as screws. The link 6 extends downwardly through the structure 9 and supports the lower bite pad at its lower end.

FIG. 4 shows a modified door closing arrangement, with a spiral spring 5a, similar to the mainspring of a small mechanical clock, with its inner end secured to the hinge pin 8, which is in turn secured against rotation with respect to its supporting lugs on the mask. The outer end of spring 5a engages the lower edge of window 4.

I claim:

1. In a welder's protective face mask including an opening defining a field of view for the wearer,
   (a) a door provided with a semitransparent window and means including a hinge adjacent the lower side of said door for supporting said door on the mask for movement between a closed position covering said opening, wherein the upper edge of said door is further from the outside front surface of the mask than the lower edge, and an open position exposing said opening,
   (b) means resiliently biasing said door to its closed position,
   (c) an upper bite pad secured to and disposed inside the mask in position for engagement by the upper front teeth of the wearer, and
   (d) a lower bite pad provided with means supporting it inside the mask below said upper bite pad for engagement by the lower front teeth of the wearer,
   (e) said last mentioned supporting means including a movable link connecting said lower bite pad to said door for upward movement toward said upper bite pad in opposition to said biasing means for opening said door in response to jaw closure movement of the weater.

* * * * *